(12) United States Patent
Hill

(10) Patent No.: US 6,751,811 B1
(45) Date of Patent: Jun. 22, 2004

(54) ELASTOMERIC TENSIONING SYSTEM FOR HEAD AND EAR MOUNTED EYEWEAR

(76) Inventor: Joe D. Hill, 1641 E. Calle Del Cielo, Tucson, AZ (US) 85718

( * ) Notice: Subject to any disclaimer, the term of this patent is extended or adjusted under 35 U.S.C. 154(b) by 0 days.

(21) Appl. No.: 10/444,027

(22) Filed: May 22, 2003

(51) Int. Cl.$^7$ .................................................. A61F 9/02
(52) U.S. Cl. .......................................... 2/453; 351/155
(58) Field of Search .......................... 2/10, 12, 6.3, 6.7, 2/453, 209.13, 424; 351/155, 158

(56) References Cited

U.S. PATENT DOCUMENTS

| | | | | |
|---|---|---|---|---|
| 2,103,006 A | * | 12/1937 | Helfenstein et al. ................ | 2/8 |
| 2,187,932 A | * | 1/1940 | Leo ................................... | 2/8 |
| 2,245,990 A | * | 6/1941 | Loud .............................. | 2/453 |
| 2,588,553 A | * | 3/1952 | McWethy ......................... | 2/8 |
| 2,700,158 A | * | 1/1955 | Hans ................................. | 2/8 |
| 4,541,125 A | * | 9/1985 | Phillips ........................... | 2/10 |
| 4,616,367 A | * | 10/1986 | Jean et al. ..................... | 2/452 |
| 4,712,254 A | * | 12/1987 | Daigle ............................ | 2/452 |
| 4,811,430 A | * | 3/1989 | Janusz ............................ | 2/452 |
| 4,852,189 A | * | 8/1989 | Duggan .......................... | 2/452 |
| 4,885,808 A | * | 12/1989 | Carpenter ...................... | 2/452 |
| 4,901,374 A | * | 2/1990 | Van der Woude .............. | 2/453 |
| 5,105,475 A | * | 4/1992 | Lynd et al. ..................... | 2/10 |
| 5,239,703 A | * | 8/1993 | Nordin et al. .................. | 2/10 |
| 5,752,280 A | * | 5/1998 | Hill ................................ | 2/453 |
| 6,481,025 B2 | * | 11/2002 | Hill ............................... | 2/453 |

\* cited by examiner

Primary Examiner—Gary L. Welch
(74) Attorney, Agent, or Firm—Mark Ogram

(57) ABSTRACT

A curved optical eye shield removably attached to a single set of arms that connect to an elastomerically operated tensioning system that is formed by two pulleys separated by a rotating armature held in place by a mounting mechanism. The eye shield rotates from a normal viewing position to an out of viewing position above the forehead. The elastomerically operated tensioning system uses a to apply clockwise tension to keep the eye shield held firmly in the viewing position, and when the eye shield is manually lifted toward the out of viewing position above the forehead, tension is applied to the reverse direction to keep the eye shield held firmly in the out of view position.

19 Claims, 6 Drawing Sheets

ELASTOMERIC TENSIONING SYSTEM FOR HEAD AND EAR MOUNTED EYEWEAR

BACKGROUND

This invention relates to athletic sunglasses with a head mounted elastomerically powered tensioning system used to rotate a lens from the viewing position in front of the eyes, to a non-viewing position above the forehead.

Outdoor athletes today are more cognizant than ever of the need to wear sunglasses as a protective barrier from the elements. Sunglasses shield the eyes from accidental invasion of foreign objects, and provide protection from the sun's ultraviolet A, 315 to 400 nanometers, and ultraviolet B, 280 to 315 nanometers, radiation levels.

Although sunglasses have been around for a long time, the basic design remains the same. Two earpieces that attach to a lens frame, that attaches to a nosepiece. Unfortunately, the shape and construction of the human head does not lend itself well to attaching ordinary sunglasses to its protrusions.

Typical sunglasses have earpieces that fit around the ears, and provide a pulling force to keep the nosepiece from sliding down the nose. The nosepiece resists this pulling force by digging into the bridge of the nose. The head feels this opposition of forces whenever sunglasses are worn. The result of these two opposite forces is sore ears and a sore nose. This is one of the problems that is solved by this invention.

The other problem of ordinary sunglasses is the inability to conveniently remove and stow the sunglasses from the viewing position when conditions require. One such condition is the wiping of perspiration from around the eyes during the heat of athletic competition, or simply the need to temporarily remove the sunglasses from the viewing position. Ordinary sunglasses require a place to be stowed during these conditions, and this is another problem solved by this invention. The outdoor athlete needs a sunglasses system that will a.) provide a tensioning system that will keep the sunglasses comfortably in place even during rigorous physical activity, b.) have the ability to quickly and easily rotate the sunglasses out of the line of sight to wipe perspiration from around the area of the eyes and then quickly and easily rotate back into the line of sight, even during the physical activity, and c.) provide easy adjustability for properly locating the sunglass lens and frame to the face.

With regard to using tensioning systems to hold the sunglasses in place, the prior design of U.S. Pat. No. 4,885,808 to Carpenter, issued Dec. 12, 1989, is indicative of the simple flip up approach of using a coiled spring tension device to hold the sunglasses in place. This arrangement also allows the sunglasses to be rotated into and out of the line of sight of the wearer. However, this design is fragile because of the single tiny flip up mechanism used to attach the eyepiece to the headband. This one fragile attachment point would allow even the smallest of impacts experienced during a sports activity to drive the eye pieces into the wearers eyes and face, posing an unacceptable risk of damage.

With regard to the ability to quickly and easily rotate the sunglasses into and out of the line of sight of the wearer, reference is made to U.S. Pat. No. 4,616,367 to Jean, issued October 1986, U.S. Pat. No. 4,712,254 to Daigle, issued December 1987, and U.S. Pat. No. 4,811,430 to Janusz, issued March 1989, as being indicative of the approaches used to hide the eyepieces in a headband to remove them from the line of sight of the wearer. This approach is not only cumbersome and time consuming for the hands to operate, but more importantly, it drastically limits the size and shape of the eyepieces that can be used because of the need to fit inside the headband when not in use. Since these eyepieces are too small and too flat to adequately follow the contours of the head and face, unfiltered sunlight as well as foreign objects are allowed to reach the eyes from the sides and bottoms of the eyepieces.

A later design to solve the problem of protecting the eyes from unfiltered sunlight and foreign objects was shown by U.S. Pat. No. 4,852,189 issued to Duggan in August 1989, by using a one-piece wrap around eyepiece held in place by a hook and loop attachment of the headband. Although the eyepiece gave better eye protection, it was still cumbersome and unwieldy to operate by requiring two hands to change the position of the eyepiece.

A more logical design to provide a rotating eyepiece was provided by U.S. Pat. No. 5,105,475, issued to Lynd on Apr. 21, 1992, by providing a wrap around eyepiece that rotates up and down by means of two arms attached to a cap headband. However, no tensioning system was provided to keep the eyepiece firmly in place in the two desired positions. And finally, the eyepiece had to rotate into a cap bill, thus limiting its travel, making the design unsuitable for a vigorous sport like basketball.

Another visor related design was made with U.S. Pat. No. 5,239,703, issued to Nordin et al in August 1993. This positional visor arrangement has two obvious drawbacks. The first is the pivot end of the journalling pin not being secured, which allows the journalling pin to slip out of the journalling opening when the visor is in either the up or down position. The second drawback is the obvious sliding friction required to expand the journalling opening for the journalling pin to rotate. Large bending moments are generated almost instantaneously during the first small movement of the journalling pin since the maximum rigidity of the journalling opening is located in the radiused corners. There is no smooth gradual increase of the forces created during operation.

A cap visor related design was made with U.S. Pat. No. 4,541,125, issued to Phillips in September 1985. However, there is no tensioning system to raise and lower the eyeshield, plus a fragile single attachment and rotation point for the eyeglasses makes this design unsuitable for aggressive sports. Even a mild impact in the area of the rotation attachment point could send the eyeglasses into the eyes and face of the wearer.

A similar design of U.S. Pat. No. 4,901,374, issued to Van der Woude in February 1990 is also based upon the single fragile attach and rotate point and same lack of a tensioning system to raise and lower the eyeshield.

A welder's eyeshield was invented with U.S. Pat. No. 2,588,553, issued to McWethy in May 1948, and U.S. Pat. No. 2,700,158, issued to Larsen in January 1955, that rotated a protective shield into and out of the wearers line of sight. The design however, has no tensioning device to raise and lower the eyeshield, but instead uses the wearer's chin to perform this function. This design is not only cumbersome, but also limited in its applications in sports.

A similar invention, U.S. Pat. No. 2,245,990, issued to Loud in June 1941 was used to rotate a protective eyeshield by means of a single hinge point and springs to assist raising the eyeshield. The use of the long coiled springs provides tension in only one direction. Tension is provided to assist the upward rotation of the eyeshield, but provides no assistance in the lowering of the eyeshield, thus the design must use snap catches on each side to keep the eyeshield from springing upward during line of sight use.

U.S. Pat. No. 2,187,932, issued to Cornell in January 1940 was a more efficient use of the spring by having the spring not only provide force to raise the eyeshield, but also to provide force to lower and hold the eyeshield in the viewing position. The drawback of using a spring-operated system is the bulky nature of their design. Springs do provide tension, but at the expense of precious available space around the forehead. To provide a sleek, compact design for the fashionable sports sunglasses market, the required tension must be supplied by a smaller and more efficient method than longitudinal coiled springs.

A similar approach, but a more complex design, was used in U.S. Pat. No. 2,103,006, issued to Helfenstein et al in Dec. 21, 1937. The springs were used to balance the welding hood in a desired viewing position, rather than provide force to snap the protective lens into and out of the viewing position. This design also required the considerable bulk and space inherent in the use of longitudinal coiled springs.

U.S. Pat. No. 5,752,280, issued to Joe D. Hill in May 1998 incorporated improvements to this design concept. However, this design also has deficiencies that have prevented the design concept from reaching its maximum efficiency in the operation of the tensioning system.

Specifically, the O-ring described in the referenced patent must travel a circuitous rout around two arms and bend around as many as four direction changing guides to perform its function. The efficiency loss of the O-ring in this configuration, measured as ounces of force at the attach point of the arm to the lens, that is, force available to lift the lens, has caused the retract mechanism to exert only 45% to 50% of the force available by the simpler more efficient proposed invention.

Also, the O-ring design itself is deficient in maximizing the force available to lift and lower the lens. This simple O-ring design does not incorporate the advantages of multiple segments located inside the middle area of the O-ring. By having a single continuous body, space is wasted in the interior area of the O-ring that could be used to provide more force for the same occupied area by adding additional reinforcing material. Also, without interior reinforcements the O-ring experiences stretching on only one side of its circumference when in operation. When the stretching reaches the O-ring's stretch limit on the O-ring's stretched half with increased tension, and the opposite half shrinks with reduced tension, it suddenly and rapidly moves to relieve the unbalanced condition and returns to a more evenly distributed stress condition. This condition is then repeated as the O-ring continues to traverse around the pulleys. These sudden movements diminish the smoothness of the operation as the O-ring is stressed performing its function.

The referenced patent also includes a single arm version, which is more efficient than a two arm version, that is not only burdened by the same O-ring deficiencies described above, but also suffers from an additional design shortcoming. The O-ring in the described single arm version is forced to bend around a stationary post used as the pivot point of the arm that attaches to the lens. This bending of the O-ring around a stationary non-rotating post induces efficiency losses that can be measured at the end of the arm where it attaches to the lens. Measurements taken indicate a loss of 30% of the lift force when the O-ring has to bend around the described post, as compared to an O-ring that does not have to bend around such a post, with all other conditions being equal.

Another solution is described in U.S. Pat. No. 6,481,025 entitled "Elastomeric Tensioning System for Head and Ear Mounted Eyewear", issued to Joe D. Hill on Nov. 19, 2002. While this patent cures the problems already listed and discussed with regard to O-ring efficiency, it suffers from other limitations, specifically friction generated by asymmetrical forces applied by the O-ring to the arm. The referenced patent has the H shaped elastomeric tensor attached between the pulley and the arm pulley, applying force along a plane some perpendicular distance removed from the plane of the arm pivot point, rotating around the arm post. This perpendicular distance between the two mentioned planes, multiplied by the force exerted by the H shaped elastomeric tensor, creates a moment arm that bends the arm outward or away from the head mount support. This problem is further magnified by multiplying this bending force being applied to the arm pulley, by the distance between the arm pulley and the arm pivot point, and the result is the H shaped elastomeric tensor is expending a significant percentage of its force trying to pry the arm off of the arm post, rather than using that force to raise and lower the protective lens eyeshield. The increase in friction between the arm and the arm post, plus the H shaped elastomeric tensor efficiency loss created by the asymmetrical application of force to the arm pulley, makes this design flawed. Any attempt to increase O-ring force to raise and lower the lens would also require increase size or strength of the associated parts to counteract the accompanying undesirable bending moments, creating a classic viscous circle design problem.

With the recent upsurge of interest in sports, a real need has developed for new and innovative designs for athletic sunglasses that realistically provide the comfort, protection, and style demanded by the modern athletes.

SUMMARY OF THE INVENTION

The present invention provides for a variety of attributes, including, but not limited to:

(a) a soft, lightweight, comfortable, open cell moisture absorbent synthetic polymer foam material to help support the tensioning system on the head of the wearer;

(b) a lightweight one piece contoured tinted optical quality eyeshield that is curved to closely emulate the shape of the face, thereby protecting the eyes from unfiltered sunlight as well as the introduction of foreign objects;

(c) a tensioning system to rotate the eyeshield into and out of the viewing position that is simple, efficient, lightweight, and economical compared to springs, cams, latches and other bulky mechanical systems used in previous patents;

(d) a head mounted elastomerically operated tensioning system that applies force to keep the eyeshield securely in place in the normal viewing position, then decreases the force to zero as the eyeshield is manually lifted to the equilibrium position toward the forehead, then applies force in the opposite direction to snap the eyeshield up to the out of viewing position without further manual assistance;

(e) a head mounted elastomerically operated tensioning system that applies force to keep the eyeshield securely in place in the out of viewing position above the forehead, then decreases the force to zero as the eyeshield is manually pushed down to the equilibrium position toward the forehead, then applies force in the opposite direction to snap the eyeshield down to the normal viewing position with out further manual assistance;

(f) an elastomeric H shaped tensor for operating a tensioning system that provides more force per square inch of area due to the addition of an H shaped reinforcement area to the interior area, unlike previously used standard O rings with vacant interior areas;

(g) an elastomerically operated tensioning system that operates without bending the elastomeric H shaped tensor around obstructions in its path during its operation, as compared to previous patents, thus increasing efficiency;

(h) an elastomerically operated tensioning system that rotates the protective eyeshield with a smooth, fluid, continuously variable force that simulates the feel of a hydraulic movement;

(i) a simple, compact adjustability system that not only adjusts the placement of the protective eyeshield in relation to the wearers nose and face, but also allows the protective eyeshield to be easily replaced with a different color or style of protective eyeshield, unlike previous patents using complex and costly screws, threaded shafts, adjustment wheels, sliding plates and other devices;

(j) a nosepiece that can be snapped into and out of the protective eyeshield, providing additional adjustability of the protective eyeshield to the face of the wearer by having the capability of using different sizes and shapes of nosepieces;

(k) an elastomerically operated tensioning system on each side of the head and connected to the protective eyeshield by means of a single arm on each side of the protective eyeshield, thus approximately doubling the efficiency of operation as compared to previous patents using pairs of arms on each side of the head;

(l) an elastomerically operated tensioning system on each side of the head, connected to the protective eyeshield by means of a single arm on each side of the protective eyeshield and this single arm being connected to the eyeshield with a solid non pivoting connection, creating a simpler more efficient connection between eyeshield and tensioning system;

(m) pivoting, adjustable elastic strap for the head mounted tensioning system that will pivot, or rotate, to automatically assume the proper fitting angle between the elastic strap and the back of the head;

(n) a head mounted system that allows the nose piece of the protective eyeshield to comfortably rest on the nose of the wearer without the stresses applied by elastic straps of conventionally designed eyewear frames pulling the nosepiece into the nose.

(o) an elastomerically operated tensioning system that incorporates two pivot point mounts on each of the two arms, so total elastomeric tensor force of each arm is divided in half and applied equally to each of the two pivot point mounts, unlike previous patents having total elastomeric tensor force applied to a single pivot point mount on each arm.

(p) an elastomerically operated tensioning system that applies elastomeric tensor force to arm pulley through a centerline between two pivot point mounts of arm, eliminating undesired bending moments of arm, unlike previous patents that apply elastomeric tensor force to arm pulley located above centerline of single pivot point mount, resulting in undesired bending moments of arm.

(q) an elastomerically operated tensioning system that uses combination of head mount support post and cover post to mount the two pivot point mounts of each arm, eliminating less sturdy, higher friction snap lock arm rivet used in single pivot point mount designs in previous patents.

(r) an elastomerically operated tensioning system that applies elastomeric force along a centerline connecting pulley and arm pulley, via between two pivot point mounts of arm, eliminating sideward thrust created by bending moments of single pivot point arm designs with pulley above centerline of single pivot point arm in previous patents.

(s) an elastomerically operated tensioning system which uses the two pivot point mount design to create a more compact enclosure that decreases its protrusion above the headmount support by one third of previous patent.

(t) an elastomerically operated tensioning system which uses a cover to not only provide one of the two arm pivot point posts for additional structural strength, but also to cover from view the internal operation of the elastomerically operated tensioning system, creating a smooth, compact, streamlined, modern appearance that is pleasing to the eye, and absent in previous patents.

The invention, together with various embodiments thereof are more fully explained by the accompanying drawings and the following description thereof

REFERENCE NUMERALS IN DRAWINGS

20—Wearers head
22—Head mount support
24—Pivoting adjustable elastic strap
26—Pivotal elastic strap attachment
28—Elastic strap snap lock pivot rivet
30—Snap lock pulley rivet
32A—Exterior arm pivot point mount
32B—Interior arm pivot point mount
33—Cover
34—Arm, left and right mirror image
36—Protective lens eyeshield
38—H shaped elastomeric tensor
40—Arm pulley
42—Nose piece
44—Lens frame
46—Pulley 48—Adjustment slider
50H—Foam insert head mount support system
52—Cover lock pin
54—Support fence pin hole
56—Arm post, head mount support
57—Arm post, cover
58—Pulley post
60—Elastomerically operated tensioning system
62F—Female adjustment stops
62M—Male adjustment stop
64—Lens assembly
66—Pivotal elastic strap assembly
68—Upper stop
70—Lower stop
72—Support fence

DESCRIPTION OF DRAWINGS

Figure 1:
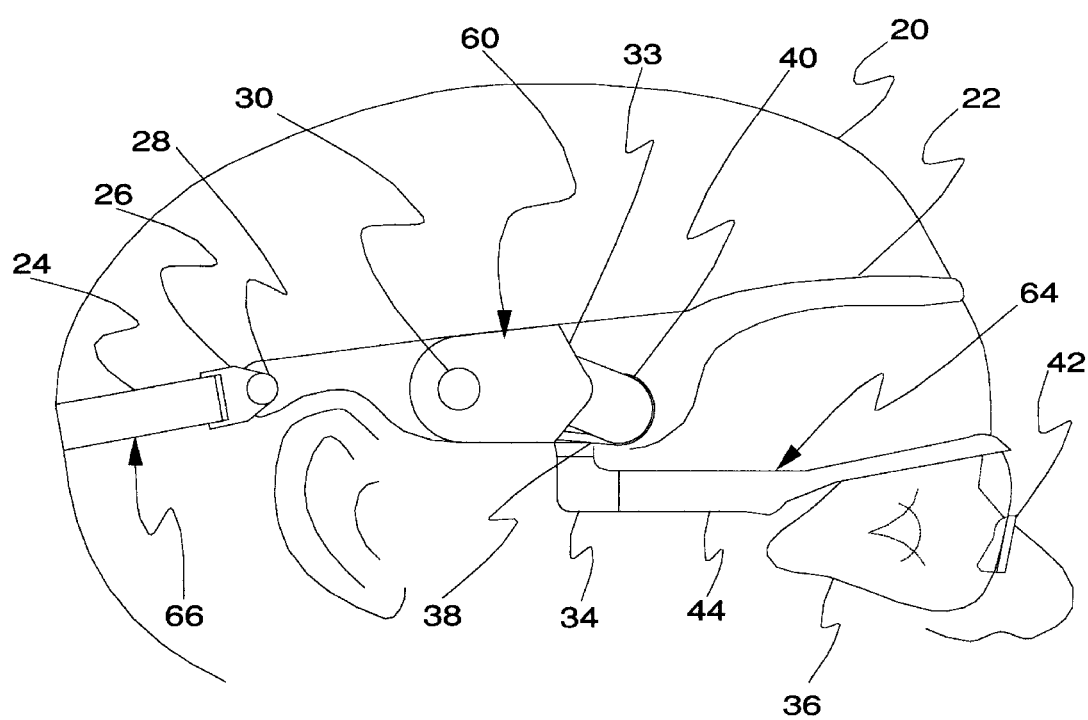
FIG. 1 is a side view of the present invention installed on the head of the wearer with the eyeshield down in the normal viewing position.
Figure 2:
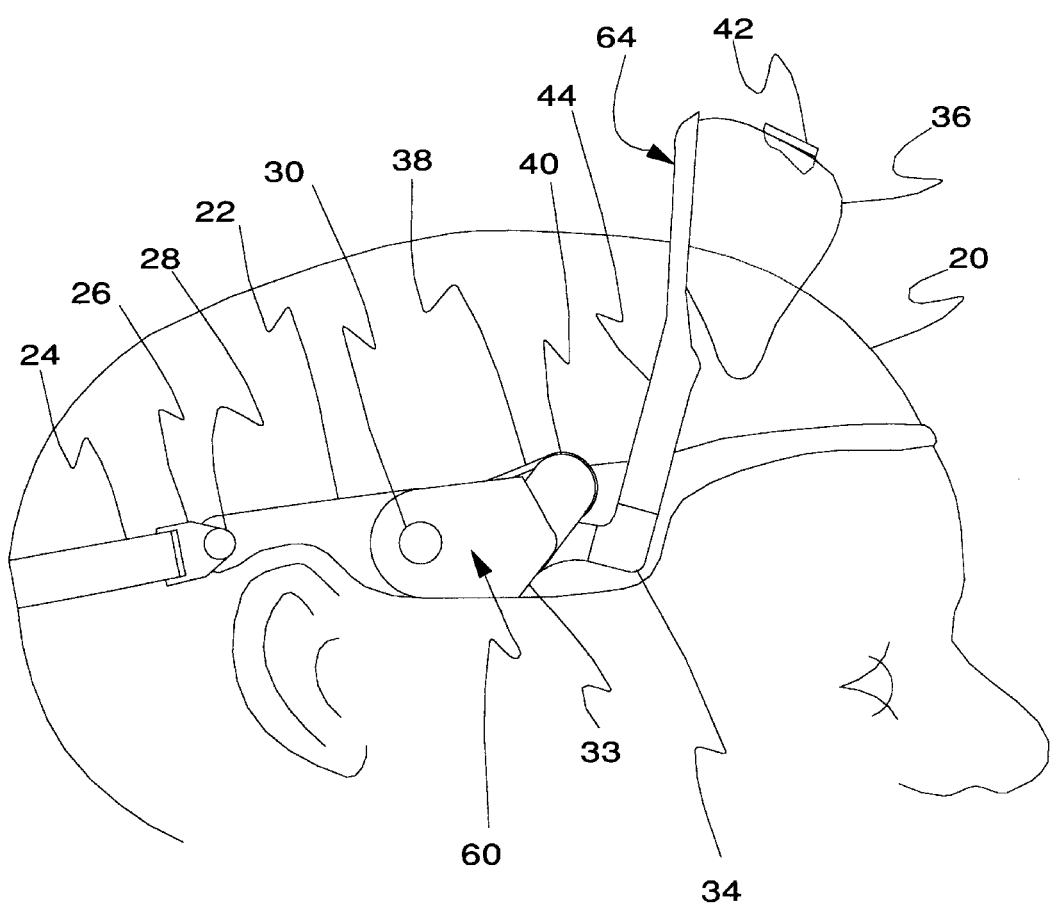
FIG. 2 is a side view of the present invention installed on the head of the wearer with the eyeshield in the out of viewing position.

FIG. 1 shows the basic invention secured on the head of the wearer (20) in the viewing position. FIG. 2 shows the basic invention secured on the head of the wearer (20) in the out of viewing position. The invention consists of four basic parts: head mount support (22), FIG. 5, elastomerically operated tensioning system (60), FIG. 1 and FIG. 6, lens assembly (64), FIG. 5, and pivoting adjustable elastic strap assembly (66) FIG. 5.

Figure 5:
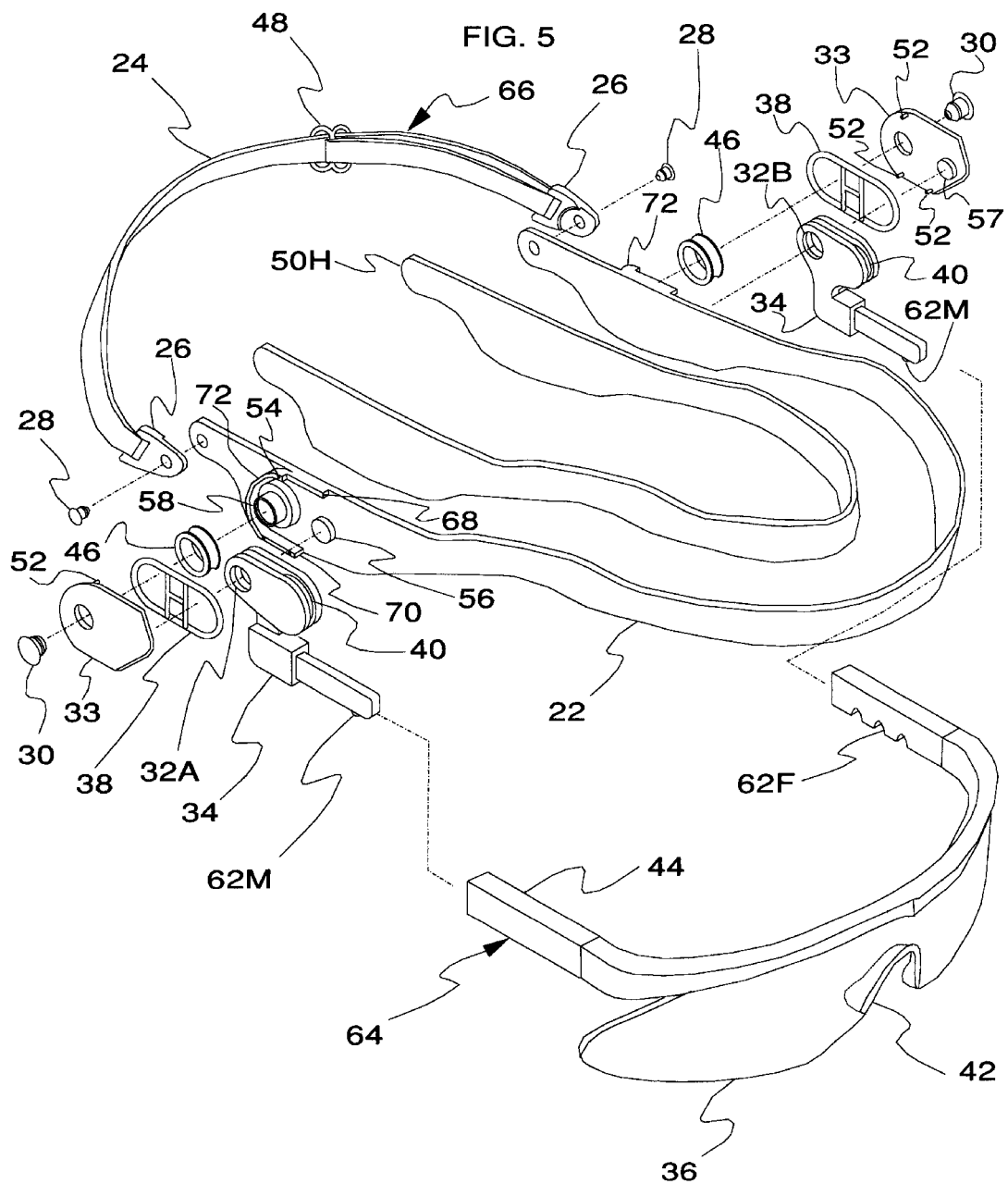
FIG. 5 is an exploded view illustrating how the elastomeric tensioning system is assembled to a head mount support, as well as the elastic strap, foam insert, and the adjustability feature of the lens frame.

Referring to FIG. 5, head mount support (22) is a one piece plastic injection molded part 0.060 inches thick, 14 inches long, and contoured to ergonomically and comfortably fit the head of the wearer without obstructing the ears, eyes, or nose. Three protrusions are located near each end: arm post, head mount support (56), pulley post (58), and support fence (72). The two ends of support fence (72) serve as upper stop (68) and lower stop (70) for limiting rotation of arm (34) when installed on arm post, head mount support (56) and arm post, cover (57). Pulley (46) is installed on pulley post (58). At each extreme end of head mount support (22) is a hole to accept and lock in place elastic strap snap lock pivot rivet (28) used to attach pivotal elastic strap assembly (66) to head mount support (22).

Figure 4:
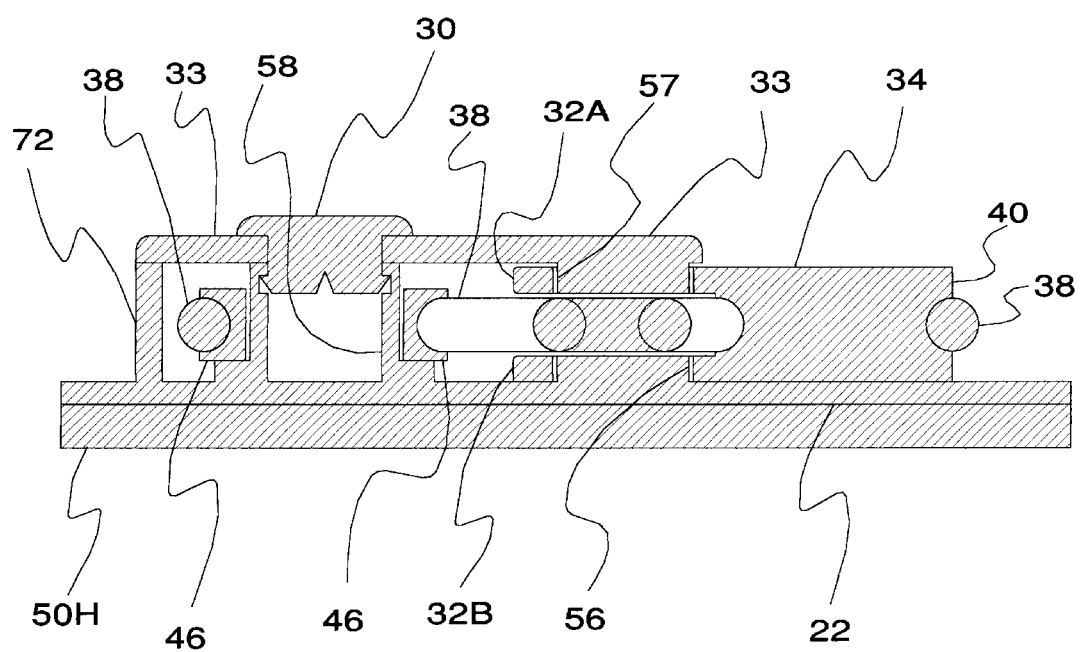
FIG. 4 is a cross-section view showing details of the construction of the elastomeric tensioning system midway in its travel.

Referring to FIG. 4, pulley post (58) has an internal groove that is injected molded into the interior wall for the specific task of capturing and locking into the respective associated protruding ring of snap lock pulley rivet (30). The locking occurs when snap lock pulley rivet (30) is pushed into pulley post (58), compressing the protruding ring area until encountering the corresponding groove area, at which time the protruding ring snaps open again, locking into the groove. The 0.43 inch diameter, 0.040 inch thick head of snap lock pulley rivet (30) secures cover (33) onto support fence (72), engaging three lock pins (52), FIG. 5, into corresponding three support fence pin holes (54), FIG. 6, and positioning arm post, cover, (57) to engage into exterior arm pivot point mount (32A) of arm (34), while arm post, head mount support (56) is engaged into interior arm pivot point mount (32B) of same arm (34), and holding pulley (46) in place onto pulley post 58. As FIG. 4 illustrates, this arrangement allows H shaped elastomeric tensor (38) to not only traverse back and forth between exterior arm pivot point mount (32A) and interior arm pivot point mount (32B) without interference during operation of elastomerically operated tension system (60), which reduces frictional loses experienced by previous designs that had to bend an O-ring around a stationary pivot post around which the arm had to rotate, but more importantly, places pulley (46), exterior and interior arm pivot point mounts (32A and 32B), and arm pulley (40) in line along a single centerline. This arrangement allows force generated by H shaped elastomeric tensor (38) to be applied through the centerline of arm (34), between the two exterior and interior arm pivot point mounts (32A and 32B) of arm (34), of arm pulley (40), and of pulley (46), eliminating bending moments to arm (34). Previous patents caused undesirable bending moments to the arm due to a single pivot point mount being located some distance below centerline of the elastomeric tensor connecting the pulley with the arm pulley, creating bending moments to the arm, the end effect being the elastomeric tensor trying to bend the arm off of the single pivot point post. Cover (33) also hides from view the internal workings of the elastomerically operated tensioning system (60), creating a smooth, compact, modern appearance for esthetic purposes.

Again referring to FIG. 5, the interior surface of head mount support (22) is covered with foam insert (50H) held in place with an adhesive layer between foam insert (50H) and head mount support (22). Foam insert (50H) is an open cell, perspiration or water absorbent, lightweight polyester foam 0.125 inches thick and cut to the same size and shape as head mount support (22). The composition of foam insert (50H) provides a friction grip with the head of the wearer for additional stability of the elastomerically operated tensioning system (60), is soft, comfortable, conforms to the shape of the wearers head, restricts and absorbs perspiration that may enter the area of the eyes and dries quickly after use or when washed.

Figure 6:
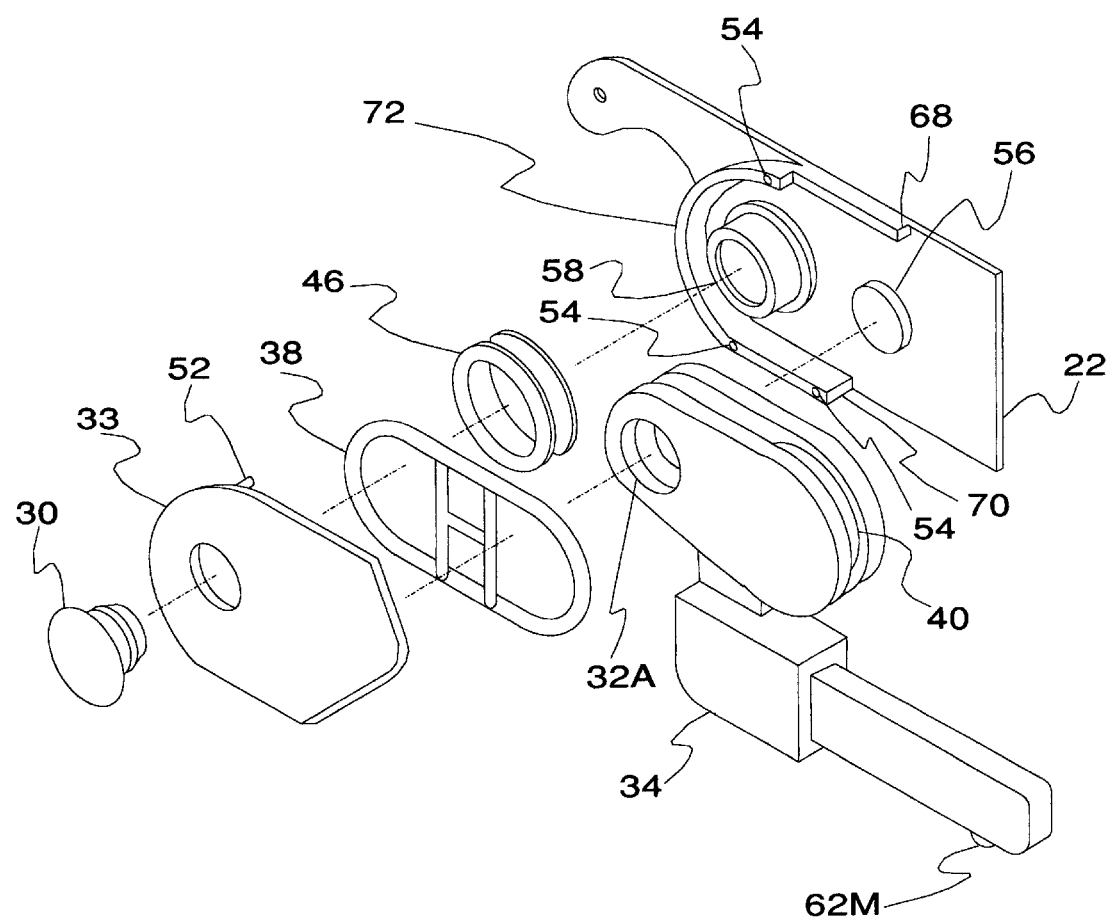
FIG. 6 is an exploded view illustrating how the elastomeric tensioning system is assembled to a head mount support section, typical for both sides of the head of the wearer.

FIG. 6 shows an exploded isometric view of elastomerically operated tensioning system (60), consisting of five parts: pulley (46), H shaped elastomeric tensor (38), arm (34), cover (33), and snap lock pulley rivet (30). It should be pointed out that arm pulley (40) is a fixed integral part of arm (34) and is injection molded as a single continuous part, as is cover lock pin (52) a part of cover (33), and as are support fence pin hole (54), support fence (72), pulley post (58), and arm post, head mount support (56) integral parts of head mount support (22).

FIG. 5 shows an exploded view of how elastomerically operated tensioning system (60) is assembled to head mount support (22) by means of arm post, head mount support (56) and pulley post (58). Pulley (46) is inserted onto pulley post (58). Interior arm pivot point mount (32B) of arm (34) is inserted onto arm post, head mount support (56). H shaped elastomeric tensor (38) is installed around pulley (46) and arm pulley (40). Cover (33) is installed onto support fence (72) engaging three cover lock pins (52) into corresponding three support fence pin holes (54) FIG. 5, 6, and arm post, cover (57) into exterior arm pivot point mount (32A) of arm (34). Snap lock pulley rivet (30) is inserted through cover (33) into pulley post (58) locking into place to complete assembly, typical for both sides. All parts are injection molded.

H shaped elastomeric tensor (38) is an injection molded polymer 1.20 inches in overall length, 0.60 inches in overall width, and has 0.100 inch diameter cross section, providing 425 grams of tension force for a 0.125 inch extension. The H shaped reinforcement interior of the design adds a longitudinal rigidity that resists twisting or bending of the interior area. Also more force per square inch of area is realized by adding reinforcement to the middle interior area, making more efficient use of available interior tensor space, a critical capability for operation in small, limited space areas.

FIG. 5 also shows how elastomerically operated tensioning system (60) is attached to lens assembly (64) by means of inserting arm (34) into lens frame (44). Female adjustment stops (62F) resides in the interior female portion of lens frame (44) which mates with male adjustment stop (62M) that resides on arm (34), typical both sides, providing the adjustability feature of lens assembly (64). Lens frame (44) is an injection molded plastic part.

Lens frame (44) has protective lens (36) attached by means of an interlocking design permanently secured by mechanical means. Protective lens (36) is a one piece curved polycarbonate type plastic shield of optical quality, and shaped to conform to the forehead, nose, and cheekbone areas of the face. Protective lens (36) can be clear for protection against the invasion of foreign objects into the eyes, but is versatile enough to use a variety of tinted lenses for outdoor applications to protect the eyes from UV A and UV B radiation from the sun as well. The application will dictate the thickness of protective lens (36), but 0.060 inches has proven to be a good balance between strength and weight.

Nose piece (42) is secured to protective lens (36) by means of a u-channel shaped groove injection molded as an integral part of nose piece (42), and snaps into place in a corresponding shape in the middle of protective lens (36). Nosepiece (42) is a soft, lightweight injection molded part that provides support for protective lens (36) as well as a device to properly locate protective lens (36) relative to the face of the wearer.

Again referring to FIG. 5, also attached to head mount support (22), is pivotal elastic strap assembly (66), consisting of adjustment slider (48), pivoting adjustable elastic strap (24) secured by means of pivotal elastic strap attachment (26) at each end, through which elastic strap snap lock pivot rivet (28) is inserted.

Pivoting adjustable elastic strap (24) is made of a polyester expandable weave material 0.080 inches thick, 0.400 inches wide, and 11 inches long before assembly. Adjustment slider (48) FIG. 5 is sewn into position to provide adjustment capability, and pivotal elastic strap attachment (26) is sewn into position at each of the two ends, through which elastic strap pivot rivet (28) is inserted to secure a completed elastic strap assembly (66) to head mount support (22).

Referring to FIG. 1 and FIG. 2, the uniqueness of the invention is the joining of lens assembly (64) to head mount support (22) by means of elastomerically operated tensioning system (60) in such a way that the joining creates a blended, well balanced apparatus that, with the touch of a finger, raises and lowers protective lens (36), with such a smooth continuously variable force that the operation can best be subjectively described as having a hydraulic feel.

The use of a single rotating arm (34) with two arm pivot point mounts (32A, 32B) on each side of head mount support (22) reduces the complexity of elastomerically operated tensioning system (60) to a minimum of three moving parts, and at the same time, approximately doubles the force available to rotate lens assembly (64) as compared to previously patented two arm and four arm designs with single pivot point mount.

Referring to FIG. 5, pulley (46) rotates around fixed pulley post (58), while interior arm pivot point mount (32B) of arm (34) rotates around arm post, head mount support (56) of head mount support (22), and exterior arm pivot point mount (32A) of arm (34) rotates around arm post, cover (57) of cover (33). Upper stop (68), and lower stop (70) at the two ends of support fence (72) limits the rotation of arm (34) to the viewing and the non-viewing positions. Support fence (72) also serves the function of a structural stiffener to support the base of pulley post (58) and the base of arm post, head mount support (56) from forces applied by the H shaped elastomeric tensor (38) through arm pulley (40) of arm (34), and pulley (46). Cover (33) provides arm post, cover (57) to engage into exterior arm pivot point mount (32A) of arm (34), as well as additional structural stiffening of support fence (72) through three cover lock pins (52) of cover (33) inserted into three corresponding support fence pin holes (54) of support fence (72). Snap lock pulley rivet (30) is used to secure cover (33) onto support fence (72), and hold pulley (46) in place on pulley post (58).

H shaped elastomeric tensor (38) is installed and resides in the groove of pulley (46) and in the groove of arm pulley (40). Since arm pulley (40) is a fixed and permanent part of arm (34), only pulley (46) rotates when the elastomerically operated tensioning system (60) is in operation. This tensioning system design is simple itself with only three moving parts: pulley (46), arm (34), and H shaped elastomeric tensor (38). This design is simple, efficient, lightweight, and economical compared to springs, cams, latches and other bulky mechanical systems. When H shaped elastomeric tensor (38) is elastically elongated from its normal non stressed state for installation, a tension or force is applied to pulley (46) and arm (34) by H shaped elastomeric tensor (38) trying to return to its normal non stressed state. The ability of H shaped elastomeric tensor (38) to consistently return to its normal non stressed state without plastic deformation is described here as its memory. The composition of the polymer used to injection mold H shaped elastomeric tensor (38) has a memory measured in years of product operation, and applies consistent force to arm (34) even through a measured 5,000 operations of elastomerically operated tensioning system (60). One of the benefits of this design is the ability to change the composition of H shaped elastomeric tensor (38) and as a result, directly change the operational characteristics of elastomerically operated tensioning system (60) as a whole. As might be expected, the possible applications of this ability are numerous.

Figure 3:
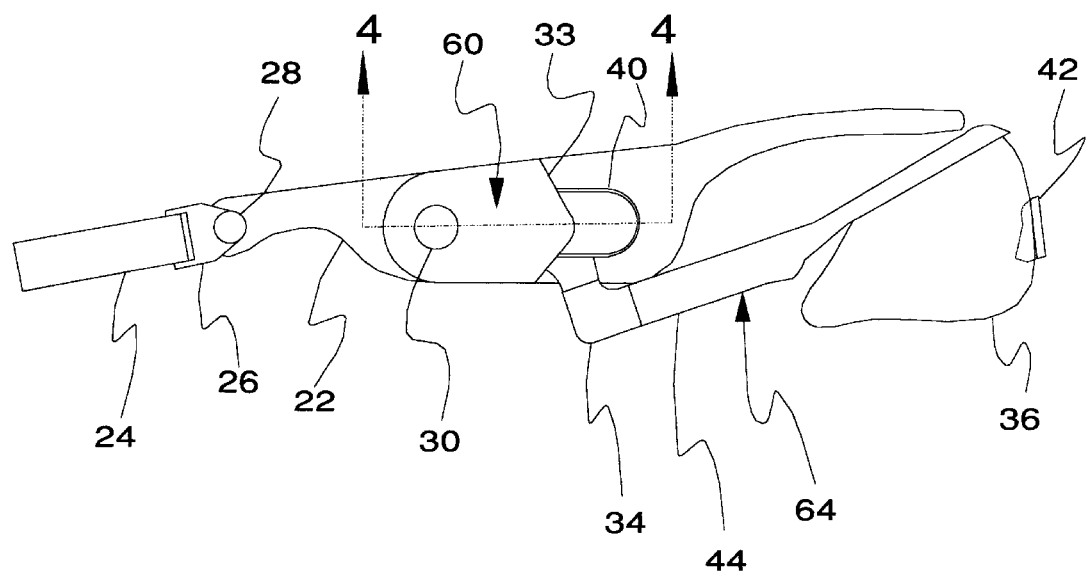
FIG. 3 is a view of the present invention midway between the normal viewing position and the out of viewing position, indicating the location of a cross sectional view.

Since pulley (46) can only rotate around stationary pulley post (58), and arm (34) can only rotate around stationary arm post, head mount support (56), and arm post, cover (57), this leaves only arm pulley (40) with the ability to pivot, or traverse radially due to its location being cantilevered 0.48 inches from the pivot point of arm post, head mount support (56), and arm post, cover (57). This arrangement creates the ability of H shaped elastomeric tensor (38) applying a moment to arm (34) in all positions except when pulley (46), arm post, head mount support (56); arm post, cover (57), and arm pulley (40) are in straight center line alignment as in FIG. 3. Referring to FIG. 3, 4, 6, the position of arm pulley (40) with regard to a straight center line passing through the center points of snap lock pulley rivet (30), arm post, head mount support (56); arm post cover (57), and extending beyond arm pulley (40) will determine the strength and direction of the moment applied by H shaped elastomeric tensor (38). If arm pulley (40) is below the centerline as in FIG. 1, a clockwise moment is being applied to arm (34) and the lens assembly (64) is being rotated down to the viewing position. If arm pulley (40) is above the center line as in FIG. 2, a counterclockwise moment is being applied to arm (34) and the lens assembly (64) is being rotated upward to the out of viewing position. If arm pulley (40) is on the centerline as in FIG. 3, the moment applied to arm (34) is zero and lens assembly (64) is in a balanced condition.

However, the weight of lens assembly (64) cantilevered on the end of arm (34) has a significant effect on the operation of elastomerically operated tensioning system (60) and must also be accounted for in the design. As shown in FIG. 1, the distance that arm pulley (40) is displaced from the centerline in the viewing position is approximately one half of the distance arm pulley (40) is displaced from the centerline in the out of viewing position in FIG. 2. The reason for the difference is a greater moment, or longer moment arm, is required to over come gravity, or the weight of lens assembly (64) to snap lens assembly (64) up to the out of viewing position. Likewise, less moment, or shorter moment arm, is required to snap lens assembly (64) down to the viewing position with the aid of gravity or the weight of lens assembly (64) assisting the movement. Although the designed differences might seem subtle or insignificant, the effects on the operation of elastomerically operated tensioning system (60) are substantial.

Again referring to FIG. 1, the beginning of a typical cycle in the operation of elastomerically operated tensioning system (60) begins with the lens in the viewing position and H shaped elastomeric tensor (38) applying a clockwise moment to arm (34), against lower stop (70), keeping lens assembly (64) held down firmly in place.

With the touch of a finger, lens assembly (64) is manually rotated upward, reducing the clockwise moment as the lens progresses toward the neutral position. As lens assembly (64) reaches the neutral position as shown in FIG. 3, the clockwise moment is reduced to zero. As lens assembly (64) passes through the neutral position, the finger is removed as the moment applied to arm (34) begins increasing in the opposite or counterclockwise direction and elastomerically operated tensioning system (60) takes over the task of rotating lens assembly (64) toward the out of viewing position. As lens assembly (64) moves closer toward the out of viewing position shown in FIG. 2, the counterclockwise moment continues to increase until arm (34) encounters upper stop (68) completing the first half of the cycle. In this position, lens assembly (64) is held firmly in the out of viewing position.

Again, with a touch of a finger, the process is repeated in reverse order, ending with lens assembly (64) held firmly in the viewing position when arm (34) contacts lower stop (70).

The distinctive shape of H shaped elastomeric tensor (38) was the result of the need to design a tension device that would meet two design goals: first, to smoothly deliver a continuously variable force without sudden movements of pulley (46) and arm (34), and second, to deliver a minimum of 425 grams of tension force with a 0.125 inch elastic elongation, and still fit within an operational area of 0.60 inches wide and 1.50 inches long.

Referring to FIG. 5 with regard to the first design goal, as arm (34) rotates around arm post head mount support (56) and arm post, cover (57), arm pulley (40) rotates in relation to pulley (46), even though arm pulley (40) is an integral part of arm (34). This situation causes a non reinforced O-ring to increase in tension on the side opposite the direction of rotation, and decrease in tension on the side of the direction of rotation. To restate in simple terms, one side of a non reinforced O-ring stretches with increased tension, and the other side shrinks with decreased tension, causing a non reinforced O-ring to twist and bend. This condition increases until a non reinforced O-ring exerts enough force on pulley (46) to overcome the inherent friction between pulley (46) and pulley post (58), and pulley (46) suddenly and quickly rotates to equalize the tension on the two sides of a non reinforced O-ring. This process then continues to repeat, causing sudden and quick movements of arm (34) as it completes its rotation. To eliminate these jerky motions, the H shaped elastomeric tensor (38) was designed with the distinctive H shaped reinforcement area interior to its circumference. The H shaped reinforcement adds lateral and longitudinal rigidity and absorbs the momentary distortions like a shock absorber. The net result is a smooth, consistent application of force that eliminates the sudden quick movements inherent in a non reinforced O-ring.

With regard to the second design goal, the addition of the H shaped reinforcement area interior to H shaped elastomeric tensor (38) circumference, was the most efficient way to produce the required 425 grams of tension force without increasing the dimensions of pulley (46), arm pulley (40), arm (34), or the O-ring itself beyond the allowable working area. The additional H shaped material provides more force per square inch of area by increasing the rigidity of the interior area. This interior rigidity design produces additional force that is not possible from the vacant interior area of a non reinforced O-ring.

Again referring to FIG. 5, the adjustability feature of lens assembly (64) will now be discussed.

The ability of lens assembly (64) to be adjusted to the face of the wearer is accomplished with a simple and efficient design consisting of three female indentations, female adjustment stops (62F) in the two ends of lens frame (44), and the associated single 0.030 inch high protrusion, male adjustment stop (62M) located on the end of arm (34). Arm (34) is manually inserted into the associated hollow area of lens frame (44) containing female adjustment stops (62F), until the single 0.030 inch high protrusion male adjustment stop (62M) engages and locks into the first female indentation. The lens assembly is now securely locked into position until manually repositioned. This adjustment position will locate the lens assembly (64) at a maximum distance from the face of the wearer. This adjustment position is intended for the wearer with a large head. Manually pushing arm (34) further into lens assembly (64) until male adjustment stop (62M) engages the next or middle indentation of female adjustment stops (62F) will locate lens assembly (64) closer to the face of the wearer, and is intended for the wearer with an average size head. Again manually pushing arm (34) further into lens assembly (64) until male adjustment stop (62M) engages the final indentation of female adjustment stops (62F) and the shoulder of arm (34) meets the shoulder of lens frame (44) creating a smooth one piece appearance, this adjustment position places the lens assembly (64) closest to the face of the wearer and is intended for the wearer with a small head.

As a result of this design, the lens assembly (64) can also be completely removed from arm (34), and another lens assembly, with a different color or style of lens, can quickly and easily be inserted onto arm (34), greatly enhancing the versatility of the invention.

Associated with the adjustability of lens assembly (64) is nosepiece (42). Since nosepiece (42) has the ability to be snapped into and out of protective lens (36), larger or smaller nosepieces, or nosepieces of different designs can be easily interchanged. This interchangeability of nosepieces adds another adjustment capability of fitting the lens to the face of the wearer. As a result, different styles and shapes of lenses can be made to fit the face of the wearer through the selection and installation of the proper nosepiece, again enhancing the versatility of the invention.

The final operative portion of the invention is pivotal elastic strap assembly (66) shown in FIG. 5. Adjustment slider (48) is manually pulled along the length of pivoting adjustable elastic strap (24) to increase or decrease the overall length of the looped portion on one side of pivoting adjustable elastic strap (24), thereby providing a size adjustability feature capable of fitting a wide range of head sizes and shapes.

The unique feature of pivotal elastic strap assembly (66), is the ability to pivot up and down relative to head mount support (22), thereby automatically adapting to any head shape or size. This pivoting action is accomplished by inserting elastic strap snap lock pivot rivet (28) through pivotal elastic strap attachment (26) secured to each end of pivoting adjustable elastic strap (24), and locking into the corresponding hole in each end of head mount support (22). Since the hole in pivotal elastic strap attachment (26) is larger than the diameter of elastic strap snap lock pivot rivet (28), the entire pivotal elastic strap assembly (66) is free to rotate about the axis of elastic strap snap lock pivot rivet (28), automatically pivoting to the correct angle to fit the wearers head.

In the simplest of terms, the invention is comprised of four basic parts: the elastic strap assembly, the lens assembly, the head mount system, and the elastomerically operated tensioning system. The purpose and theory of operation for the elastic strap assembly, the lens assembly, and the head mount assembly is straightforward and unambiguous.

The theory of operation of the elastomerically operated tensioning system can best be described as the application of forces generated whenever a tension device, such as the familiar rubber band, is deformed from its natural state. In this case, the elastomerically operated tensioning system uses an H shaped tensor specifically designed for this application, but the principle remains the same.

When the H shaped tensor is elastically elongated to be installed on a freely rotating rear pulley on a fixed post behind the arm, and on the arm pulley, a force is applied to both pulleys by the H shaped tensor trying to return to its natural state. Since the rear pulley rotates on a fixed post, it cannot pivot, and since the arm can pivot, and the arm pulley is located some distance from the arm's pivot point, a moment is applied to the arm pulley. When the arm pulley is in straight centerline alignment with the rear pulley and the arm pivot point, the moment is zero and the arm is in a balanced condition. This is because the net moment arm of the arm pulley has zero perpendicular length relative to the centerline passing through the arm pivot point.

The position of the arm pulley relative to the arm pivot point determines the direction and magnitude of the moment being applied to the arm. When the lens assembly is in the viewing position as in FIG. 1, there is a clockwise moment being applied to the arm holding the lens assembly down firmly in place. When the lens assembly is in the out of viewing position as in FIG. 2, a reverse or counter clockwise moment is being applied to the arm holding the lens assembly firmly up in the out of viewing position.

As the arm moves to and from the positions just described, the moments applied to the arm by the H shaped tensor increases as the arm pulley swings further away from the straight center line, and decreases as the arm pulley swings closer to the straight center line, and changes direction when the arm pulley crosses the straight center line.

This smooth continuous changing of the applied forces gives a smooth, fluid operation of the elastomerically operated tensioning system.

The above description contains many specifications, these should not be construed as limitations on the scope of the invention, but rather as an exemplification of one preferred embodiment thereof. Other variations are possible. For example, the elastomerically operated tensioning system could be used for raising and lowering welding glasses, safety glasses, reading glasses, medical magnification lenses, motorcycle or bicycle helmet shields, and virtual reality displays.

The head mount areas could be used for logos or advertising, with all the possible color and graphic combinations. Since all parts are injection molded, the parts could be made of different colors to mix or match to produce any conceivable color scheme.

The entire invention could be scaled down to fit smaller heads of teen and pre-teen age athletes.

What is claimed is:

1. An eye glass comprising:
  a) a headband configured to be secured to a user's head;
  b) a lens assembly rotatably connected to said headband and having an eye shield therein; and,
  c) a tensioning mechanism having,
    1) a pulley assembly having,
      A) a first pulley,
      B) an armature having a first end and a second end, said armature having a second pulley rotatably secured to the second end thereof, the second end of said armature secured to said lens assembly,
      C) a bracket mechanism securing said first pulley and the first end of said armature to said headband and,
    2) an elastic band being substantially oval and having a central support, said elastic band stretched between said first pulley and said second pulley such that said elastic band encourages selective rotation of said lens assembly relative to said headband to: a first resting state within a user's line of sight, and a second resting state outside the user's line of sight.

2. The eye glass according to claim 1, wherein said bracket includes an external cover such that said first pulley and the first end of said armature are both sandwiched between the headband and said external cover.

3. The eye glass according to claim 2, wherein said first pulley and the first end of said armature are allowed to rotate between said headband and said external cover.

4. The eye glass according to claim 3, wherein said headband includes:
  a) a stiff head mount support adapted to be placed over a user's forehead; and,
  b) an elastic strap connected to said stiff head mount support and adapted to extend around a back of a user's head.

5. The eye glass according to claim 4, wherein said elastic band contacts only said first pulley and said second pulley.

6. The eye glass according to claim 5, wherein said elastic band is generally oval and includes a central support extending from side to side of said elastic band.

7. The eye glass according to claim 3, wherein said eye shield is detachable from said lens assembly.

8. The eye glass according to claim 7, further including a corrective vision lens connected to said eye shield.

9. The eye glass according to claim 8,
  a) wherein said eye shield includes a nose piece; and,
  b) wherein said corrective vision lens is secured to said nose piece.

10. The eye glass according to claim 9, wherein said corrective vision lens is removable from said eye shield.

11. The eye glass according to claim 8, wherein said corrective vision lens is positioned such that, when said eye glass is worn by a user, said corrective vision lens are positioned between the user and the eye shield.

12. An eye protective apparatus comprising:
   a) a headband configured to be secured to a user's head, said headband having a first pulley;
   b) an armature having a first end and a second end, the first end of said armature secured to said headband, said armature having a second pulley secured to the second end thereof;
   c) a lens assembly connected to the second end of said armature; and,
   d) an elastic band stretched between said first pulley and said second pulley such that maximal relaxation of said elastic band occurs at a first state and a second state.

13. The eye protective apparatus according to claim 12, further including an external cover such that said first pulley and the first end of said armature are both sandwiched between the headband and said external cover.

14. The eye protective apparatus according to claim 13, wherein said first pulley and the first end of said armature are allowed to rotate between said headband and said cover.

15. The eye protective apparatus according to claim 14, wherein:
   a) said first state positions said eye shield within a user's line of sight; and,
   b) said second state positions said eye shield outside the user's line of sight.

16. The eye protective apparatus according to claim 15, wherein said eye shield is detachable from said lens assembly.

17. The eye protective apparatus according to claim 15, further including a corrective vision lens connected to said eye shield.

18. An eye glass comprising:
   a) a headband having,
      1) a stiff head mount support adapted to be placed over a user's forehead, and
      2) an elastic strap connected to said stiff head mount support and adapted to extend around a back of a user's head;
   b) a lens assembly having an eye shield therein; and,
   c) a tensioning mechanism having,
      1) a first pulley,
      2) an armature having a first end and a second end, said armature having a second pulley rotatably secured to the second end thereof, the second end of said armature secured to said lens assembly,
      3) a bracket mechanism securing said first pulley and the first end of said armature to said headband, and,
      4) an elastic band stretched between said first pulley and said second pulley such that said elastic band encourages selective rotation of said lens assembly relative to said headband to: a first resting state within a user's line of sight, and a second resting state outside the user's line of sight.

19. The eye glass according to claim 16, further including a corrective vision lens connectable to said eye shield via a nose piece.

* * * * *